(12) United States Patent
Ninh et al.

(10) Patent No.: US 11,478,124 B2
(45) Date of Patent: Oct. 25, 2022

(54) SYSTEM AND METHODS FOR ENHANCED AUTOMATED ENDOSCOPY PROCEDURE WORKFLOW

(71) Applicant: DocBot, Inc., Irvine, CA (US)

(72) Inventors: Andrew Ninh, Fountain Valley, CA (US); Peter Crosby, San Juan Capistrano, CA (US); William E. Karnes, Irvina, CA (US); Efren Rael, Belmont, CA (US); John Cifarelli, Oyster Bay, NY (US)

(73) Assignee: DocBot, Inc., Irvine, CA (US)

( * ) Notice: Subject to any disclaimer, the term of this patent is extended or adjusted under 35 U.S.C. 154(b) by 0 days.

(21) Appl. No.: 16/897,114

(22) Filed: Jun. 9, 2020

(65) Prior Publication Data
US 2021/0378484 A1    Dec. 9, 2021

(51) Int. Cl.
*A61B 1/00*    (2006.01)
*G16H 15/00*   (2018.01)
(Continued)

(52) U.S. Cl.
CPC ...... *A61B 1/00009* (2013.01); *A61B 1/00045* (2013.01); *A61B 1/04* (2013.01);
(Continued)

(58) Field of Classification Search
CPC ......... A61B 1/00009; A61B 1/04; A61B 1/31; A61B 1/00045; G16H 70/40; G16H 30/40; G16H 10/20; G16H 50/20; G16H 15/00; G16H 50/70; G16H 70/20; G06T 7/0012; G06T 2207/10016; G06T 2207/20081; G06T 2207/30092; G06T 2207/10068; H04N 5/272
See application file for complete search history.

(56) References Cited

U.S. PATENT DOCUMENTS

| | | |
|---|---|---|
| 4,915,435 A | 4/1990 | Levine |
| 6,082,799 A | 4/2000 | Marek |

(Continued)

FOREIGN PATENT DOCUMENTS

| | | |
|---|---|---|
| WO | WO-2007031946 A2 | 3/2007 |
| WO | WO-2016201123 A1 | 12/2016 |

OTHER PUBLICATIONS

Karim Ghazikhanlou Sani et al., A Comparison of the Efficacy, Adverse Effects, and Patient Compliance of the Sena-Graph Syrup and Castor Oil Regimens for Bowel Preparation, Jun. 2009, School of Pharmacy Shaheed Beheshti University of Medical Sciences and Health Services, pp. 1-2 (Year: 2009).*

(Continued)

*Primary Examiner* — Robert A Sorey
*Assistant Examiner* — Kimberly A. Sass
(74) *Attorney, Agent, or Firm* — Eversheds Sutherland (US) LLP; Nicola A. Pisano; Albert K. Heng

(57) ABSTRACT

Systems and methods are provided for delivering consistent high quality, cost efficient results in fixed or mobile endoscopy facilities, without requiring the continuous real-time involvement of a fellowship trained gastroenterologist, by integrating patient specific information into decision support systems and AI/machine learning systems employed during the planning and examination phases of the endoscopy procedure.

19 Claims, 9 Drawing Sheets

(51) Int. Cl.

| | | |
|---|---|---|
| *G16H 50/70* | (2018.01) | |
| *G16H 50/20* | (2018.01) | |
| *G16H 70/40* | (2018.01) | |
| *G16H 30/40* | (2018.01) | |
| *G16H 10/20* | (2018.01) | |
| *G16H 70/20* | (2018.01) | |
| *A61B 1/04* | (2006.01) | |
| *A61B 1/31* | (2006.01) | |
| *G06T 7/00* | (2017.01) | |
| *H04N 5/272* | (2006.01) | |

(52) U.S. Cl.
CPC .............. *A61B 1/31* (2013.01); *G06T 7/0012* (2013.01); *G16H 10/20* (2018.01); *G16H 15/00* (2018.01); *G16H 30/40* (2018.01); *G16H 50/20* (2018.01); *G16H 50/70* (2018.01); *G16H 70/20* (2018.01); *G16H 70/40* (2018.01); *H04N 5/272* (2013.01); *G06T 2207/10016* (2013.01); *G06T 2207/10068* (2013.01); *G06T 2207/20081* (2013.01); *G06T 2207/30092* (2013.01)

(56) References Cited

U.S. PATENT DOCUMENTS

| | | | |
|---|---|---|---|
| 6,171,112 B1 * | 1/2001 | Clark | G16H 40/20 434/322 |
| 10,671,934 B1 | 6/2020 | Ninh et al. | |
| 2004/0249670 A1 | 12/2004 | Noguchi et al. | |
| 2005/0036668 A1 | 2/2005 | McLennan et al. | |
| 2007/0005795 A1 | 1/2007 | Gonzalez | |
| 2007/0265492 A1 | 11/2007 | Sonnenschein et al. | |
| 2007/0279521 A1 | 12/2007 | Cohen | |
| 2012/0320088 A1 | 12/2012 | Ihara et al. | |
| 2014/0031677 A1 | 1/2014 | Iftimia et al. | |
| 2015/0106123 A1 * | 4/2015 | Amarasingham | G16H 10/60 705/3 |
| 2015/0260534 A1 | 9/2015 | Shen | |
| 2015/0282749 A1 | 10/2015 | Zand et al. | |
| 2015/0374210 A1 | 12/2015 | Durr et al. | |
| 2016/0210411 A1 | 7/2016 | Mentis | |
| 2016/0364526 A1 | 12/2016 | Reicher et al. | |
| 2018/0253839 A1 * | 9/2018 | Zur | G06T 7/0012 |
| 2019/0238791 A1 | 8/2019 | Ingle | |
| 2019/0289359 A1 | 9/2019 | Sekar et al. | |
| 2019/0370963 A1 | 12/2019 | Chiu et al. | |
| 2020/0279368 A1 * | 9/2020 | Tada | A61B 1/00016 |
| 2020/0410672 A1 * | 12/2020 | Katscher | G16H 10/60 |

OTHER PUBLICATIONS

Clay Dillow, First Ever Real-Time MRI Video Captures Images of Body's Interior in Just 20 Milliseconds, 2010, Popular Science (Year: 2010).*

Anderson, et al., Prepared by ASGE Standards of Practice Committee, Endoscopy by Nonphysicians, *Gastrointestinal Endoscopy*, 69(4):767-771 (2009).

Corley, et al., Adenoma Detection Rate And Risk of Colorectal Cancer and Death, *New England Journal of Medicine*, 370:1298-306 (2014).

Day, et al., Non-Physician Performance of Lower and Upper Endoscopy: A Systematic Review and Meta-Analysis, Endoscopy: A Systematic Review and Meta-Analysis, *Endoscopy*, 46:401-410 (2014).

Greenwald, et al., Mobile Screening Units For the Early Detection of Cancer: A Systematic Review, *Cancer Epidemiol. Biomarkers Prev.*, 26(12):1679-94 (2017).

Kaminski, et al., Quality Indicator For Colonoscopy and the Risk of Interval Cancer, *New England Journal of Medicine*, 362:1795-803 (2010).

Karnes, et al., Su1642 Automated Polyp Detection Using Deep learning: Leveling The Field, Gastrointestinal Endoscopy, 85(5), Supplement, AB376-AB377 (2017).

Komaravolu, et al., Colonoscopy Utilization in Rural Areas Dy General Surgeons: An Analysis of the National Ambulatory Medical Care Survey, *Am. J. Surg.*, 218(2):281-287 (2019).

Riegert, et al., Experience of a Nurse Practitioner Performing Colonoscopy at a Tertiary Center In the United States, *J. Gastrointest. Dig. Syst.*, 5:3 (2015).

Talukdar, et al., Making Endoscopy Mobile: The Journey, *Digestive Endoscopy*, 24 (Suppl. 1): 172-174 (2012).

Urban, et al., Deep Learning Localizes and Identifies Polyps in Real Time With 96% Accuracy In Screening Colonoscopy, *Gastroenterology*, 155(4):1069-1078 (2018).

Wang, et al., Real-Time Automatic Detection System Increases Colonoscopic Polyp and Adenoma Detection Rates: A Prospective Randomized Controlled Study, *Gut*, 68:1813-1819 (2019).

Zachariah, et al., Can Artificial Intelligence (AI) Achieve Real-Time Reset and Discard Thresholds Independently of Device of Operator?, *American Journal of Gastroenterology*, 113:S129 (2018).

Zachariah, et al. Artificial Intelligence For Colon Polyp Detection: Why Should We Embrace This? *Techniques and Innovations in Gastrointestinal Endoscopy*, 22:48-51 (2020).

International Search Report & Written Opinion dated Oct. 1, 2021 in Int'l PCT Patent Appl. Serial No. PCT/US2021/036476 (0210).

* cited by examiner

SYSTEM AND METHODS FOR ENHANCED AUTOMATED ENDOSCOPY PROCEDURE WORKFLOW

FIELD OF THE INVENTION

The present invention relates generally to systems and methods for enhancing endoscopic examinations of the human body, and particularly systems and methods for augmenting colonoscopy procedures with automated decision workflow systems that improve examination quality and cost effectiveness.

BACKGROUND OF THE INVENTION

Endoscopy refers to the use of an instrument for visual examination of an internal body part. A common example of endoscopy is colonoscopy, during which a flexible tube with imaging apparatus at the distal end is inserted into a person's colon. The purpose of colonoscopy is to search for and identify abnormalities in the internal wall of the colon and, in some cases, remove them. Such abnormalities include polyps and various types of adenomas.

Screening colonoscopy remains the best-proven method to detect and prescribe early treatment for colon cancer. Clinical guidelines typically suggest that a first colonoscopy be performed at age 50, but in developed countries like the USA, only about one third of people comply with such guidelines. Increasing the compliance rate is a universal goal of the professional gastroenterology community that potentially save millions of lives. One of the major contributors to the current low ideal compliance rate is scarcity of resources, both physical and human.

Colonoscopy typically is performed by a fellowship-trained gastroenterologist. However, a shortage of gastroenterologists in the United States and globally limits access and contributes to a less than ideal compliance rate for colonoscopy in the general population. In many cases, colonoscopy facilities are not readily available or available at reasonable cost. The shortage of trained gastroenterologists also contributes to a shortage of facilities for performing colonoscopies, particularly in small and rural communities. Underutilized physical facilities are not financially viable, and therefore it is challenging to obtain sufficient investment to build new facilities.

As a result of these limitations on existing colonoscopy testing services, primary care physicians (PCP), general surgeons, nurse practitioner and physician assistants have filled the void in performing such procedures. In rural areas, general surgeons and family medical practitioners primarily fulfill the need for colonoscopy, as reported in Komaravolu S S, Kim J J, Singh S, Merchant A M, "Colonoscopy Utilization in Rural Areas by General Surgeons: An Analysis of the National Ambulatory Medical Care Survey," Am J Surg., 218(2):281-287 (2019). Nurse practitioners also can achieve similar quality measures as fellowship trained gastroenterologists, as reported in Riegert M. L. et al., "Experience of a Nurse Practitioner Performing Colonoscopy at a Tertiary Center in the United States," J Gastrointest Dig Syst 5:3 (2015).

While guidelines exist for endoscopy performed by non-physicians, the guidelines also state, "There are insufficient data to support non-physician endoscopists to perform colonoscopy and upper endoscopy." See, e.g., American Society of Gastroenterology "Endoscopy by non-Physicians" Gastrointestinal Endoscopy, (69)4:767-771 (2009). More recent surveys reveal that when "non-physicians perform endoscopic procedures, especially lower endoscopies, outcomes and adverse events are in line with those of physicians," as reported in Day L. W., Siao D., Inadomi J. M., ad Somsouk M., "Non-physician performance of lower and upper endoscopy: a Systematic Review and Meta-Analysis" Endoscopy 46:401-410 (2014).

A well-accepted measure of quality of a colonoscopy is the so-called "adenoma detection rate" (or ADR). This is a measure of the proportion of patients in whom an adenoma is detected during colonoscopy. The prevalence of adenomas in the screening age population is thought to be about 50% (i.e.: half of people screened have at least one adenoma), but typical ADR is about 25%, as reported in Corley D. A. et al "Adenoma Detection Rate and Risk of Colorectal Cancer and Death" NEJM 370:1298-306 (2014). ADR is a proven measure of risks of colorectal cancer between screenings ("interval colorectal cancer") and the ADR is inversely associated with the risks of interval cancer. See, Kaminski M. F. et al., "Quality Indicator for Colonoscopy and the Risk of Interval Cancer," NEJM 362:1795-803 (2010). The current ADR rate of 25% means that in half of screened patients an adenoma is missed. Unfortunately, quality is variable among colonoscopists and tends to be lower among PCPs and APNs.

Additionally, colonoscopies are typically performed in brick-and-mortar facilities such as surgery (endoscopy) centers and hospitals. Such procedures require a significant investment in specialized instruments and staff. The suite of materials needed to perform a complete colonoscopy procedure include an optical apparatus, such as video endoscope; an optical video monitor to view the endoscope video feed; electronic video recording and procedure documentation device; a variety of polypectomy devices, including biopsy forceps, snares, electric cautery materials, and hemostatic clips; carbon dioxide ($CO_2$); oxygen; water; anesthesia machines, supplies, and drugs; vitals monitoring equipment; disinfectant chemicals and endoscopy reprocessing and sterilization supplies; and pathology services.

Colonoscopy procedures are also labor-intensive, requiring a colonoscopist to maneuver the endoscope, an anesthetist to administer anesthesia (for procedures that require anesthesia), and an endoscopy nurse or technician to operate under the colonoscopist's supervision.

Further, due to the specialized nature of colonoscopy, it can take some time to set up the procedure room between patients. This setup time is increased if the type of procedure is changed between patients, as the type of equipment and personnel will change. Variability in setup time can reduce the efficiency of resource utilization and exacerbate the problem of insufficient resources.

In rural areas and in many geographies with emerging healthcare services, there are not enough facilities and resources to perform colonoscopies, nor enough trained personnel. Accordingly, there is a great need to provide high quality colonoscopy services to a larger population than is now possible. Chief among these challenges is the need to enable less qualified or specialized operators to achieve detection results on par with fellowship-trained gastroenterologists.

In some medical fields, technology has been used to assist lesser-skilled operators use sophisticated medical equipment. For example, U.S. Patent Application Publication No. 2017/0360402 to Jonge et al. describes a system that uses an augmented reality image overlay on an ultrasound image to guide an operator to target anatomy.

Artificial intelligence (AI) also has been used to aid evaluation of a patient's status prior to colonoscopy. For example, U.S. Patent Application Publication No. 2019/0370963 to Chiu et al. discloses a system and method for evaluating the quality of bowel preparation prior to colonoscopy and classifying an image recorded by an endoscope.

Artificial intelligence (Machine learning) approaches have been used for analysis of static images, such as X-ray mammography, CT scan or MRI. See, for example, U.S. Patent Application Publication No. 2016/0364526 to Reicher et al. Although these inventions may be useful for some applications, a fundamental requirement for endoscopic image analysis is that it be performed in real time on high resolution video (i.e.: colored images) with minimal frame lag, so that the clinician has an opportunity to fully reposition the endoscope to obtain additional images needed to evaluate any potential abnormalities.

Artificial intelligence (AI) approaches have been proposed to detect polyps in real-time with high accuracy in screening colonoscopy, as reported in Urban, G., et al., "Deep Learning Localizes and Identifies Polyps in Real Time with 96% Accuracy in Screening Colonoscopy," Gastroenterology, 155(4):1069-1078 (2018). One such approach is described in U.S. patent application Ser. No. 16/512,751, developed by some of the inventors of this application, which application is hereby incorporated by reference in its entirety. This approach has been shown in clinical studies to provide improved ADR without increasing the time or cost of a colonoscopy procedure. See, Wang P., et al., "Real-Time Automatic Detection System Increases Colonoscopic Polyp and Adenoma Detection Rates: A Prospective Randomized Controlled Study," Gut 68:1813-1819 (2019). While the use of such AI approaches will enable high-quality colonoscopies to be performed by personnel other than fellowship-trained gastroenterologists, additional options for enhancing quality and cost efficiency are required.

One approach to improving the utilization of resources in a specialized endoscopy suite is described in U.S. Patent Application Publication No. US 2007/0265492 A1, now abandoned. That application describes a specialized endoscopy suite that is set up to perform a plurality of endoscopic procedures, such that a standardized set of parameters was "pre-programmed" into the suite between patients. More specifically, the endoscopy suite includes a memory unit that stores a list of endoscopic procedures and parameters, and which can automatically adjust the controls of devices within unit, such as lighting, suction, and insufflation pressure levels. This system does not describe the use of patient demographics, the purpose of the procedure or other patient vital information to inform such adjustments.

In addition, a mobile surgery suite has been proposed to address the shortage of facilities in rural areas, as described in U.S. Pat. No. 4,915,435 to Levine, entitled "Mobile Operating Room With Pre And Postoperational Areas." That patent describes a mobile, transportable operating room capable of comprehensive surgical care, including the types of care generally performed in fixed hospital facilities. The mobile vehicle is described as a self-contained expandable van that contains essential ancillary services, including anesthesia, a sterilizing autoclave for instruments, a complete operating room, and anesthesia equipment. The mobile operating room described in that patent is designed primarily for invasive surgeries and includes a single sterile area through which both patients and medical personnel enter.

Similarly, U.S. Pat. No. 6,082,799 to Marek, entitled "Mobile Ambulatory Surgery Center," described a mobile ambulatory surgery center designed for elective, non-emergency surgical procedures, in which an expandable mobile vehicle includes designated sterile and nonsterile areas, such that patient flow protects the sterility of the operating room. In particular, mobile ambulatory surgery center includes an admitting area, where business transactions involving the patient may be handled, a changing area, a sterile operating room, a waste storage area. Patient traffic through the center enables the patient to exit the operating room while maintaining the integrity of sterile areas. This traffic pattern is not optimal for endoscopic procedures, and the patent does not describe an area for endoscope/equipment reprocessing and cleaning rooms, which must be present in an endoscopy center.

Yet another approach to mobile endoscopy suite is described in Talukdar R. and Reddy D. M. "Making Endoscopy Mobile: The Journey" Digestive Endoscopy, 24 (Suppl. 1) 172-174 (2012), in which telemedicine is employed to transfer of images and data from remote locations to a central center for reading and analysis.

Mobile endoscopy suites are available in the United States. See, for example the product offerings from EMS Mobile Healthcare (https://www.ems-healthcare.com/what-we-do/mobile-endoscopy-units/ accessed 15 Apr. 2020), the mobile endoscopy clinic from Odulair Inc. (see https://www.odulair.com/mobile-endoscopy-unit-mobile-endoscopy-suite.html last accessed 15 Apr. 2020), and the product from Mobile Healthcare Facilities LLC (https://mhcfac.com/facilities/mobile-endoscopy-facility-5316m/ last accessed 15 Apr. 2020). While these products provide mobile physical facilities for endoscopy, none solves the continuing problem of achieving consistently high quality outcomes or overcoming the scarcity of adequately trained personnel.

Notwithstanding the availability of mobile colonoscopy units, use of such units to reduce the incidence of colon cancer has not been widely adopted. On the contrary, a systematic review of the scientific literature, as reported in Greenwald, Z. R., El-Zein, M., Bouten, S., Ensha, H., Vazquez F. L. and Franco, E. L., "Mobile Screening Units for the Early Detection of Cancer: A Systematic Review," Cancer Epidemiol Biomarkers Prev, 26(12): 1679-94 (2017) found reports of only one such program—in South Africa. Accordingly, there is a long-felt need in the field to address the poor adoption of mobile screening for colonoscopy, which at least partly results from the shortage of trained personnel who can provide consistent high-quality results.

Other efforts have focused on improving the work efficiency of ancillary staff, such as nurses. For example, U.S. Patent Application Publication No. US2004/0249670 describes a system including portable terminals carried by nurses and a plurality of TV cameras that send images to a plurality of screens, thereby enabling nurses to view the status of procedures in real-time. That application does not describe integration of the viewing system with other equipment in the endoscopy room.

In view of the foregoing drawbacks of prior art endoscopy systems and methods, there remains a need for an endoscopy facility that can deliver consistent high quality without requiring the continuous real-time involvement of a fellowship-trained gastroenterologist.

There also is an unmet need for an endoscopy facility, whether located in a fixed or mobile facility, that can improve the workflow for endoscopic procedures, integrate patient specific information in the procedure planning, improve the consistency of detections, and automate patient processing to enhance patient care and cost-efficiency.

In view of the foregoing, it would be desirable to provide systems and methods to improve utilization and quality of colonoscopy suites, such that the shortage of fellowship trained gastroenterologists and the performance limitations of non-fellowship trained healthcare professionals will no longer be the limiting factor in achieving higher compliance to the colonoscopy screening guidelines.

SUMMARY OF THE INVENTION

In accordance with the principles of the present invention, systems and methods are provided for overcoming the drawbacks of prior art endoscopy systems and methods, and which deliver consistent high quality without requiring the continuous real-time involvement of a fellowship-trained gastroenterologist. The systems and methods of the invention advantageously may be employed in both fixed and mobile endoscopy suites to improve the workflow for endoscopic procedures, integrate patient specific information in the procedure planning, improve the consistency of detections, and automate patient processing to enhance patient care and cost-efficiency. The inventive systems and methods are expected to enhance patient compliance with examination guidelines, reduce cost, enhance ADR, improve patient outcomes and save lives that otherwise would be lost to colon cancer.

Described herein is an apparatus and method for automating processes for an endoscopy center to deliver consistent high-quality colonoscopy. The inventive system provides (1) automated patient intake that assesses patient preparedness, elicits information that informs the endoscopic examination and addresses patient concerns; (2) sensors that guide the patient through the endoscopy appointment; (3) decision support systems to provide data to guide endoscopy staff during the endoscopy procedure; (4) provide the endoscopist with enhanced real-time adenoma detection using an integrated endoscopic video stream informed by patient-specific information; (5) audio and/or visual sensors that assist the endoscopist during endoscopic procedures with general maneuverability, abnormality detection, and localization, and (6) a method for delivering endoscopic procedures in accordance with the present invention suitable for use in both fixed and mobile facilities.

In operation, a patient checks-in on the day of the schedule procedure using a mobile device or a patient intake kiosk located in the waiting area of the endoscopy suite. More specifically, an electronic questionnaire is presented to the patient to determine if the patient reports to have adequately prepared for the procedure the night before. The questionnaire also collects and records patient-specific information, including medical history and family history associated with the condition for which the examination is to be conducted. Using the patient information, the system may retrieve historic and current patient records from one or more databases and health information exchanges. If the patient is inadequately prepared, the procedure may be canceled. If the patient is deemed adequately prepared, the input or retrieved information may be forwarded to the endoscopy staff, for example, to prepare to perform polypectomies if the patient has history of polyps. The patient may then be directed to a specific pre-operative bay where the patient is provided information regarding the procedure, for example, by way of an informative video that is personalized for the patient based on the questionnaire responses. Based on the information regarding the procedure, the system may offer the patient a choice of anesthesia options, and alert the endoscopy staff to any such elections, the specifics of the examination, and that the patient has arrived for the procedure.

Prior to the procedure, the patient is presented an electronic form to sign to confirm informed consent. The procedure may be performed with or without anesthesia or conscious sedation, as requested by the patient. The endoscopy staff will outfit the patient with appropriate vital signs monitoring sensors, e.g., ECG and pulse oximetry probe, and the patient vital signs will be monitored and recorded during the procedure. In accordance with one aspect of the invention, the patient information input via the questionnaire, e.g., patient specific medical history and/or family medical history will be provided to decision support software to guide the endoscopist during the procedure to detect abnormalities of the type previously encountered during examinations of the patient or the patient's blood relatives. The decision support software, including by way of example statistical and machine learning algorithms, may provide to the endoscopist in real time two- or three-dimensional reconstructed representations of the anatomy, localization to indicate the position of the endoscope, directional guidance arrows to indicates turns and/or to explore poorly visualized regions, and bounding boxes indicating potential lesions or suspect abnormalities that require closer inspection. Preferably, the decision support system is an artificial intelligence (AI) system, such as a deep learning system implemented on a suitable computer system, which may be local or remote.

Data from algorithms and sensors are stored in a database and analyzed to document the complete exam. Upon completion of the procedure, a written report of the procedure is generated automatically by the system using captured data and the report is submitted for medical billing and coding, and for secure transmission to the patient in physical and/or electronic form. Data from the AI based decision support system may be used automatically to populate the procedure report, thereby reducing the need for human labor.

Upon completion of the procedure, the endoscopy operating room is cleaned. Reusable endoscopes are cleaned, reprocessed and disinfected in a cleaning device located in an adjunct room to the operating room. Alternatively, a single use endoscope may be employed to reduce cleaning and reprocessing.

Optionally, there may be an adjunct room for analysis of pathology specimens. The pathology report automatically is stored in the system database and results are included in the procedure report when available.

In accordance with one aspect of the invention, systems and software are provided to assist or automatically maneuver the endoscope, detect abnormalities and lesions such as polyps, automatically connect with networks and sensors to receive input data from the patient intake questionnaire, to document and guide the procedure, and localize the endoscope position in the organ in real-time.

A preferred endoscopy system of the invention includes a visual display. In one preferred embodiment, a video feed from the endoscopy machine is routed through the AI decision support system, which outputs a composite display including the image generated by the endoscope overlaid with the graphical information from the AI decision support system. Alternatively, a plurality of displays may be employed, a first of which shows the original video feed from the endoscopy machine, and a second that shows the video feed overlaid with data from the AI based decision support system. Other displays may be employed to show additional information, such as patient history and other data. In a further alternative embodiment, such additional information can be showed in a picture in picture (PIP) format on a single display.

The addition of an AI based decision support system to a regular endoscopy procedure allows endoscopy practitioners to maintain high-quality performance such as ADR.

The inventive endoscopy system may be located in a fixed endoscopy suite or mounted in a mobile prefabricated structure, such as a semi-trailer outfitted to function similarly to a fixed endoscopy center, and may include a patient intake area, waiting area, endoscopy operating rooms, patient recovery bays, storage and cleaning rooms, and optionally a pathology laboratory.

Further features of the invention will become apparent from the detailed description, the claims, and the drawings, which are intended for illustration only and are not intended to limit the scope of the disclosure.

DETAILED DESCRIPTION OF THE INVENTION

The present invention provides systems and methods for delivering consistent high quality, cost efficient results in fixed or mobile endoscopy facilities without requiring the continuous real-time involvement of a fellowship-trained gastroenterologist. More particularly, the inventive systems and methods improve the workflow for endoscopic procedures by integrating patient specific information into decision support systems and AI/machine learning systems employed during the planning and examination phases of the endoscopy procedure, thereby improve the consistency of detection of abnormalities, and enhancing patient care. In the following specification, reference is made in detail to specific embodiments of the invention suitable for use in endoscopic procedures such as colonoscopy. It should be understood, however, that the benefits and advantages of the present invention are equally available for other endoscopic procedures such as esophageal and airway examination.

In accordance with one aspect of the invention, system and methods are provided wherein an automated patient questionnaire is used to collect patient information during patient admission/intake. That information in turn is employed by an artificial intelligence system to aid in decision support and detection of adenomas. The addition of the AI system ensures consistent high-quality results, independent of the qualifications and experience of the person performing the endoscopy.

In accordance with another aspect of the invention, automation is provided to facilitate otherwise laborious tasks, such as: patient intake and analysis; determining whether the patient complied with bowel cleansing guidelines prior to the appointment; assessing the patient's likelihood of needing an intervention based on demographics, personal and family history, and indication of the procedure; real-time endoscope maneuverability guidance; and automated post-operative report generation and billing/coding. Automating these normally labor-intensive steps is expected to streamline the endoscopy process, improve facility efficiency, and reduce overhead and number of staff required to operate the endoscopy lab. When implemented together with tuning of the decision support system and detection system based on patient specific data, the inventive system and methods will enable endoscopy procedures to be more accessible in geographies with fewer resources and minimal access to endoscopy expertise, while maintaining a high-quality service and detection capabilities.

In accordance with yet another aspect of the invention, automated collection and analysis of data from multiple patient procedures is expected continually to improve the AI decision support system and to monitor performance.

Figure 1:
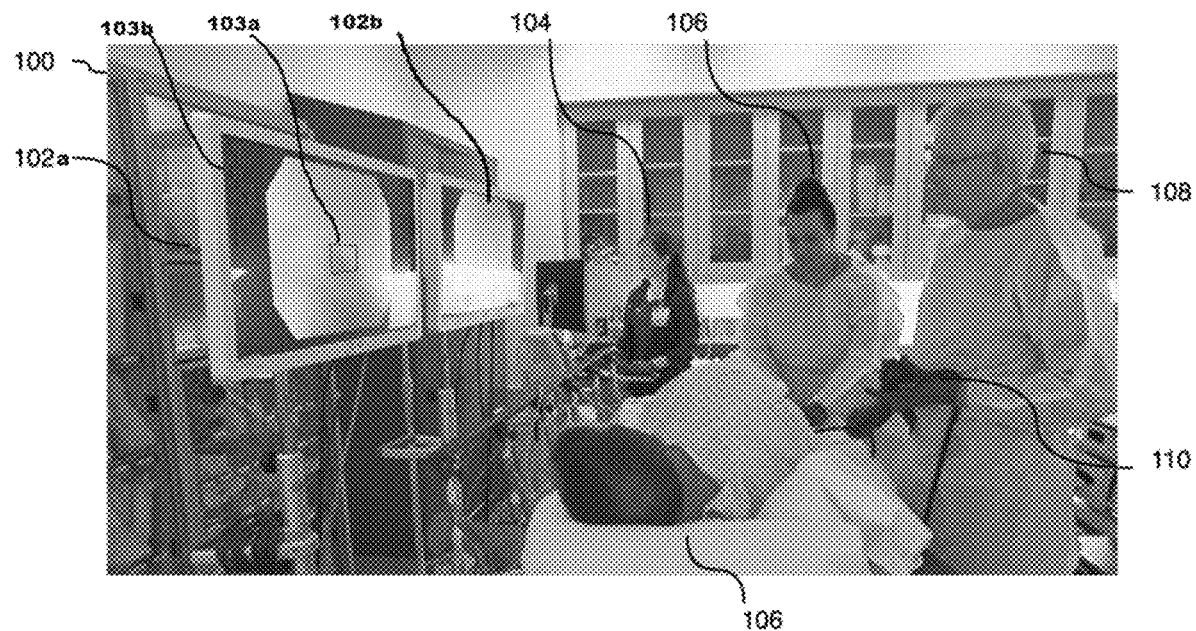
FIG. 1 depicts an endoscopy suite arranged in accordance with one aspect of the present invention, in which an endoscopist examines an image of a patient's colon with the aid of a real-time visual assistance software.

Referring to FIG. 1, aspects of the inventive systems and methods are described. Endoscopy procedure room 100 is shown in which patient 106 is being examined by endoscopist 108. Endoscopist 108 is assisted by nurse 104 and surgical technician 106. Endoscopist 108 manipulates the handle of colonoscope 110, which is inserted through the colon of patient 106 with the aid of endoscopy monitors 102a and 102b. In accordance with one aspect of the present invention, endoscopy monitor 102b provides the raw video image created from the camera signal in the colonoscope, while monitor 102a provides with real-time guidance and AI decision support overlay. In particular endoscopy monitor 102a displays the image from the colonoscope with real-time software overlay, where the overlay is generated as described in commonly assigned U.S. patent application Ser. No. 16/512,751, the entirety of which is hereby incorporated by reference. In accordance with the principles of the present invention, the AI decision support overlay is informed using patient specific information generated in part based on the patient's responses to personal and family medical history information inputted in response to an automated questionnaire and/or retrieved from the patient's medical record database. In particular, the AI decision support software can be "tuned" (e.g.: change the operating point on the Receiver Operating Characteristics (ROC) curve for optimal specificity and sensitivity) based on the pre-test likelihood determined from the patient specific information. In this manner, the endoscopist and the AI decision support software are alerted to the patient's predisposition to known abnormalities, thereby heightening the endoscopist's and AI software's search for such features in the video stream generated by colonoscope 110.

During the colonoscopy procedure, colonoscope 110 is advanced to the cecum, the region near the top of the colon at the junction with the small intestine, and then withdrawn slowly. As is conventional in such examinations, the endoscopist may apply rinse and suction to the mucosal surface during advancement to remove residual fecal matter or opaque liquid to cleanse the organ and enhance visibility. Once this process is completed and the colonoscope advanced to the cecum, colonoscope 110 is withdrawn while the endoscopist closely inspects the images of the colon surface (the mucosa). Nurse 104 and surgical technician 106 may assist during the procedure by repositioning the patient if needed, by applying pressure to the patient, monitoring patient vital signs, applying and monitoring anesthesia and sedation, and assisting with interventions. In some settings, the endoscopy procedure may be performed by the endoscopist 108 and nurse 104, without technician 106, or some other combination of medical professionals.

Real-time overlay on the endoscope video image displayed on monitor 102 (illustratively includes bounding box 103a) informs the endoscopist of color or textural changes in the mucosal surface that require closer examination. Additional textual information 103b displayed adjacent to the video image may assist endoscopist 108 to maneuver the colonoscope through spastic episodes or difficult flexures in the anatomy with minimal assistance from nurse 104 or technician 106.

Monitors 102a and 102b may be general purpose or specialized video monitors that accept any standard or proprietary video signal, including but not limited to HDMI, SDI, 3G-SDI, 6G-SDI, DVI, and DisplayPort, and optionally may be capable of additional functionality, including any of picture-in-picture (PIP), video signal loop-through, audio input, split screen, and toggling between multiple inputs.

Figure 2:
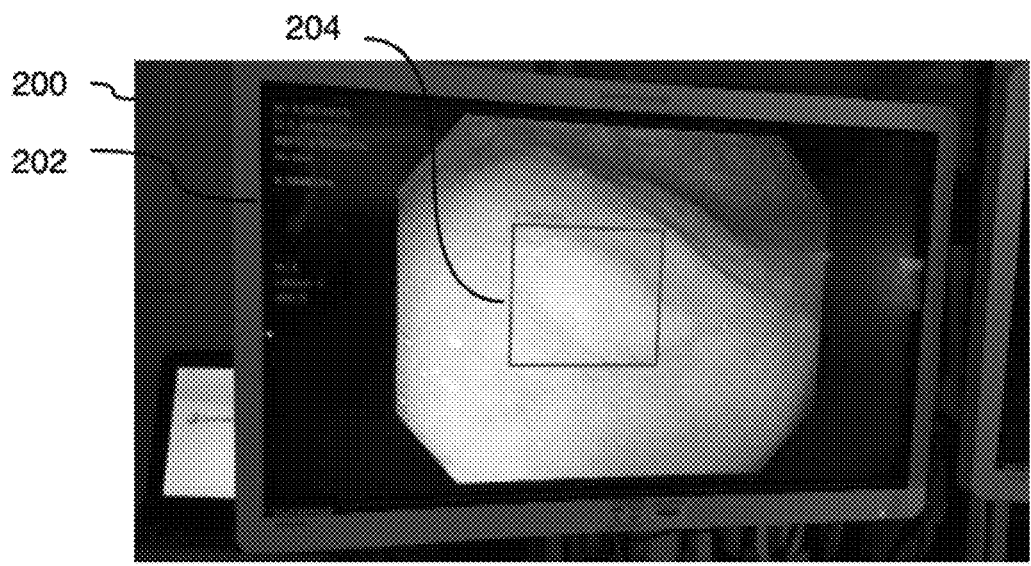
FIG. 2 is an expanded view of a user interface showing a visual aid superimposed on the video stream generated by the optical endoscope.

Referring now to FIG. 2, an exemplary display of visual guidance interface 200 presented on monitor 102a is described. The visual guidance is computed in real-time and displayed to the endoscopist during the procedure. Preferably, the visual guidance is computed in real time by an artificial intelligence (AI)/machine learning system. The interface may present any of directional arrows, bounding boxes (e.g., 103a, 204) around suspected lesions, and textual information (e.g., 103b, 202) that display information such as the real-time location of the tip of the endoscope, insertion time, withdrawal time, time when the cecum is reached, whether a maneuver such as polypectomy should be performed, and current surface visualization (e.g., as may be calculated using the "Boston Bowel Prep Score" nomenclature). Overlay 200 is preferably generated by a computer (which may be a general purpose computer or a computer specifically designed for the task) which takes sensor input such as the endoscopy video feed, other optical inputs such as ultrasound, vitals data signals, and audio signals. The computer typically includes at least a central processing unit (CPU), graphical processing unit (GPU), and memory (RAM). Endoscopy monitors 102a, 102b and overlay 200 also may provide picture-in-picture (PIP) representation of other visualization modalities, including 3D reconstruction and rendering, or other methods of localizing the tip of the endoscope in the human body.

Figure 3:
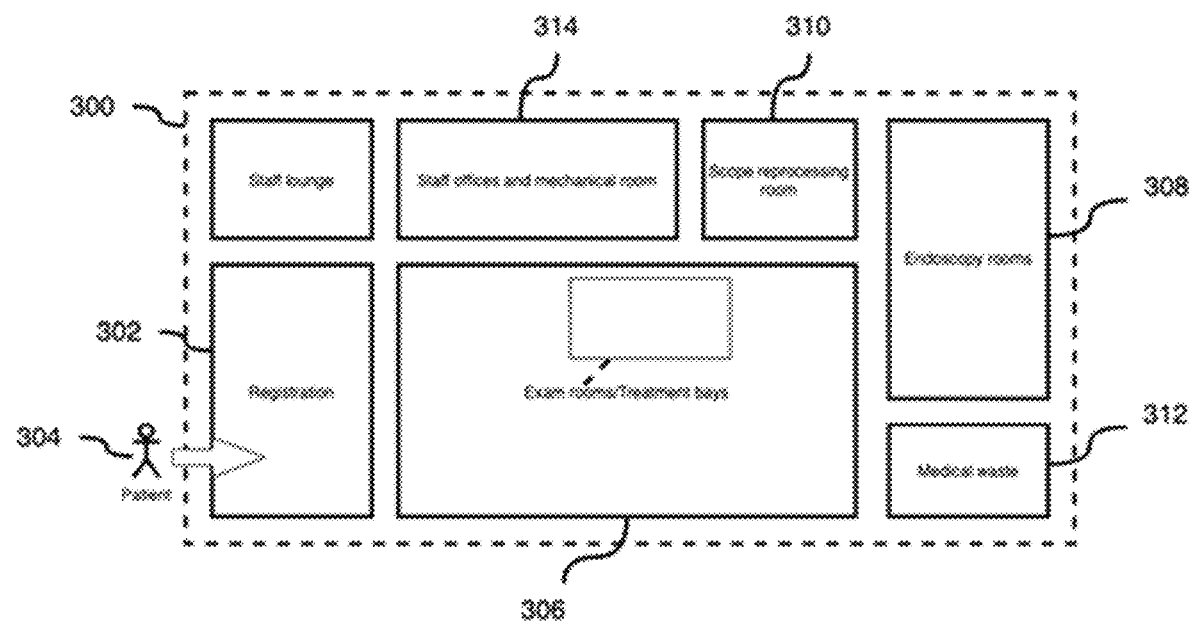
FIG. 3 is a diagram of an exemplary fixed endoscopy facility suitable for implementing the invention of the present invention.

FIG. 3 depicts floorplan 300 of an exemplary "bricks and mortar" fixed facility endoscopy center suitable for implementing the systems and methods of the present invention. Endoscopy center 300 may be a freestanding facility or part of a larger building such as a specialty clinic, surgery center, or hospital building. Typical patient flow from entry to discharge is shown by dotted line 304. A traditional endoscopy center includes patient registration area 302, where business transactions, such as data entry into patient intake forms, are conducted. Patient pre- and post-operative recovery area 306 may individual recovery bays, where patients await an endoscopy procedure and where patients return to recover from an endoscopy procedure. The patient generally is transferred from area 306 to endoscopy lab and operating rooms 308, where the procedure is performed. Endoscope cleaning, reprocessing, and storage occurs in room 310. The exemplary facility also includes medical waste disposal rooms 312 and administrative offices, staff lounge and lockers area 314.

An endoscopy center usually is associated with a pathology laboratory that receives samples for analysis by a pathologist. The pathology laboratory may be part of an endoscopy facility or may be located elsewhere. In accordance with one aspect of the present invention, results of any pathology analysis conducted on biopsied tissues preferably are linked with the patient's medical record, so that they can be retrieved for review and comparison purposes in connection with subsequent endoscopic examinations.

Figure 4:
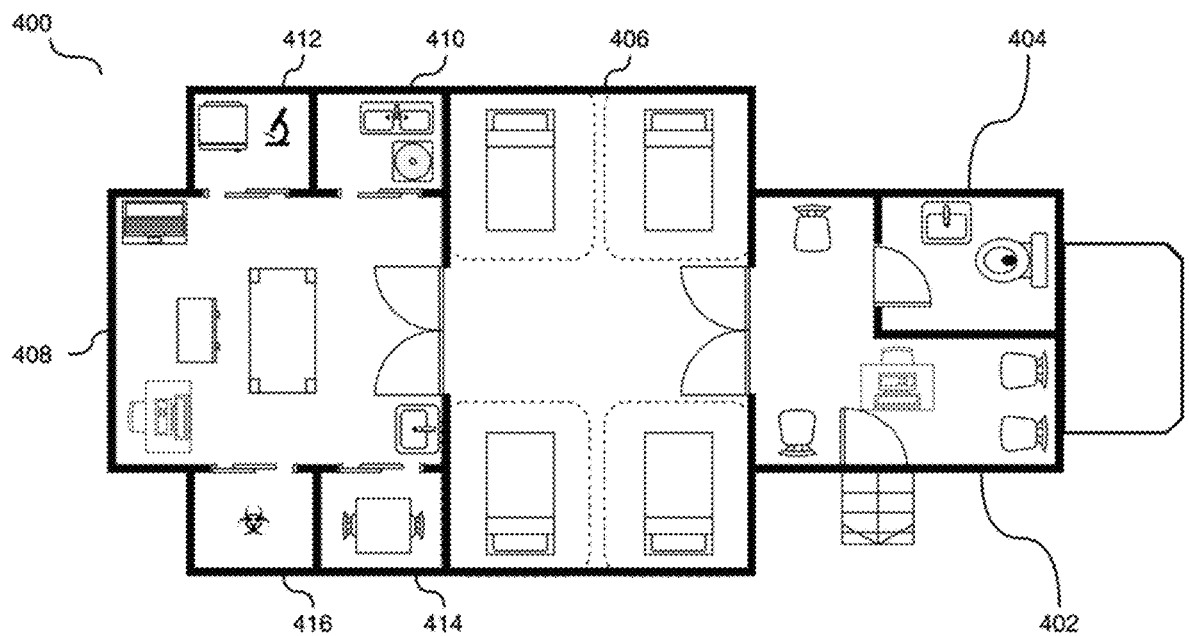
FIG. 4 is a diagram of a mobile endoscopy facility suitable for implementing the inventive system.

Referring now to FIG. 4, a floorplan for an exemplary mobile endoscopy center 400, suitable for implementing the systems and methods of the present invention, is described. Mobile endoscopy center 400 includes both sterile and nonsterile facilities and equipment located within the body of an expandable semi-trailer truck. The resources and functions available in mobile endoscopy center 400 generally are similar to fixed facility 300 described above. Specifically, mobile endoscopy center 400 includes patient waiting room/intake area 402 through which a patient enters and exits using a staircase or wheelchair lift. The bathroom and changing area 404 adjoins the waiting room/intake area. Pre- and post-operative recovery bay 406 includes at least one adjustable bed that can be surrounded by a privacy curtain. Endoscopy lab 408 has space for the endoscopic procedure, one or more display monitors, storage for surgical supplies, e.g., forceps, snares, cautery, and endoscope storage, a nurse working station, anesthesia/sedation equipment, and a sink. Endoscope reprocessing, cleaning, and disinfecting is performed at station 410. Other functions available may include pathology specimen, pathology slide reading, and storage facility 412; storage and staff lounge room 414; and medical waste storage room 416.

As will be understood by a person familiar with mobile surgical suites, mobile endoscopy center 400 may be located in a semi-trailer truck or single or multiple story prefabricated mobile structure. It will also be appreciated that the facilities provided in mobile endoscopy center 400 are exemplary, and that some facilities omitted and others added—for example, pathology laboratory 412 may be omitted and pathology samples may be transported elsewhere for analysis.

Figure 5:
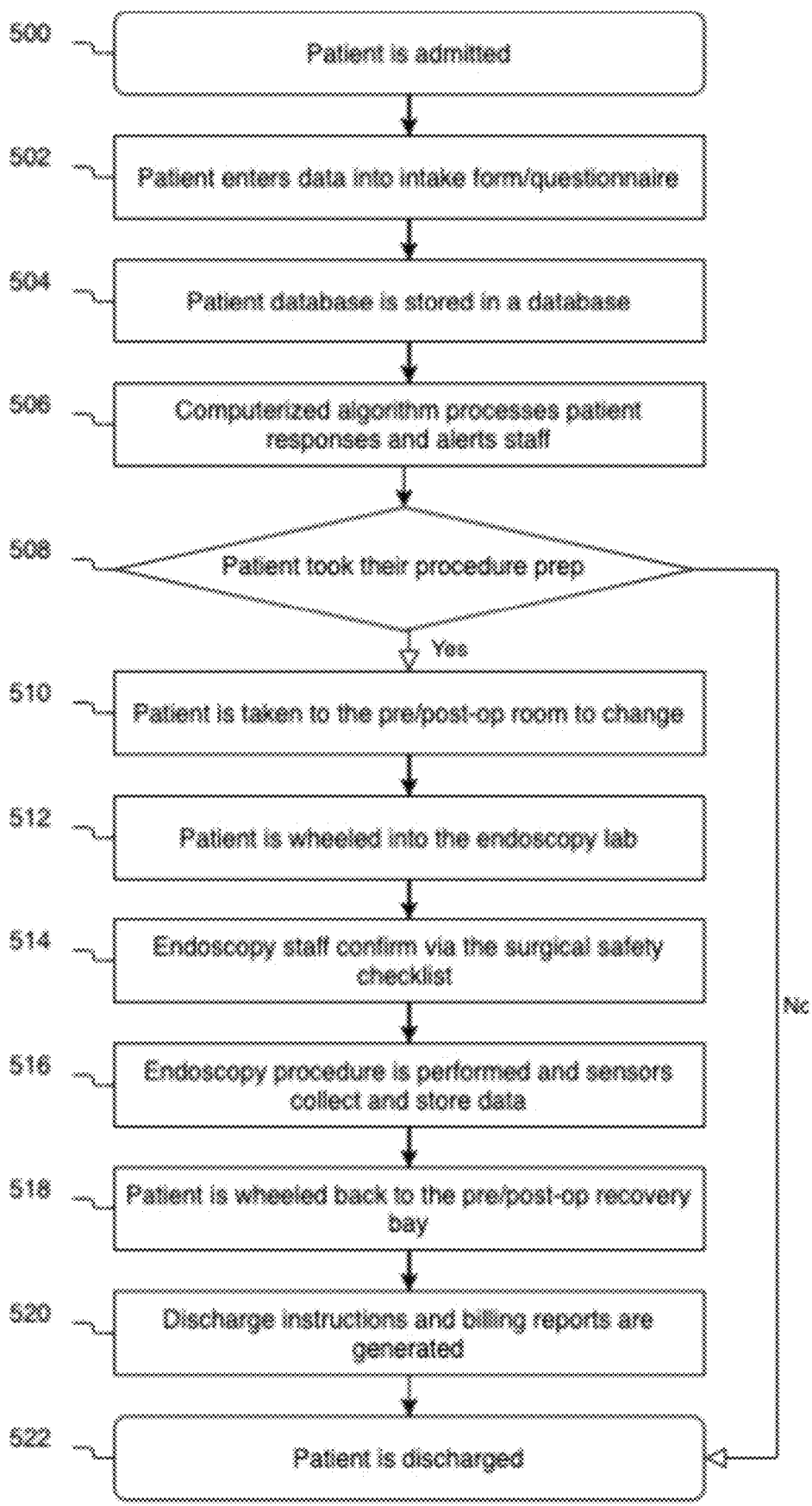
FIG. 5 is an exemplary flowchart describing the sequence of events for a patient's endoscopy appointment.

FIG. 5 provides a high-level overview of patient processing workflow for an endoscopy appointment from the time a patient is admitted until the patient is discharged. The steps set forth in FIG. 5 may be implemented in either a fixed facility, such as described with respect to FIG. 3 or a mobile facility that that described in FIG. 4. Generally, when the patient enters the facility at step 500, personal data are collected and entered in a HIPAA and GDPR privacy compliant electronic questionnaire 502, which may be implemented on paper or more preferably, on an electronic tablet device or smart phone. In some cases, at least some of the patient data may be captured and stored in advance of admission. Upon completion and submission of the electronic intake form, the patient data is sent to a local or remote (cloud) database where it is stored, at step 504.

A computerized algorithm inputs and processes the patient data, at step 506, to cross-reference historic patient records, and to search and retrieve data from external databases such as from Health Information Exchanges across multiple health information systems (HIS). The endoscopy staff then is informed that the patient's records are available and that the patient is ready in the waiting room. By inputting information such as demographic, personal and family history, and an indication for the procedure, the endoscopy staff can prepare the endoscopy unit and prepare equipment to be used during the examination. The patient questionnaire also accepts data about whether the patient has followed the colonoscopy cleaning preparation guidelines the night before, at step 508. If the patient indicates that such cleaning preparation guidelines were not observed, the patient may be immediately discharged, at step 522, and no procedure is performed.

Because in most instances the patient would have completed the necessary cleaning preparation, the patient next is alerted, at step 510, to enter the pre-/post-operating recovery area and to change into a surgical gown. At the time of the patient's procedure, the patient is wheeled on a gurney into the endoscopy lab by a nurse, at step 512. Before the patient is optionally sedated and the procedure begins, the surgical staff goes through a surgical safety checklist, at step 514. Next, the endoscopy procedure is performed, at step 516, during which a plurality of sensors monitor and record patient signals, such as audio, optical, endoscopy video, and vital signs signals. In accordance with one aspect of this invention, the sensor signals may be processed in real-time to provide decision support that aids in the safe and efficient maneuvering of the endoscope. Preferably, the real-time decision support system includes an AI (machine learning) system. Upon the completion of the procedure, the patient is wheeled back to the recovery bay, at step 518.

Data collected during the procedure may be automatically analyzed using a computer system concurrently, and post-procedure, to generate a comprehensive endoscopy report that is provided to the patient and referring physician for recordkeeping, at step 520. Preferably, the computer system that generates the report also accepts information from the decision support system, for example time of insertion, time of reaching the cecum, and withdrawal time. The report also may be used by the facility and endoscopist to bill for the procedure and may be integrated with a larger HIS or electronic medical record (EMR) or endoscopy report writer for archiving and billing. The patient then is discharged by the supervising endoscopist, at step 522.

Figure 6A:
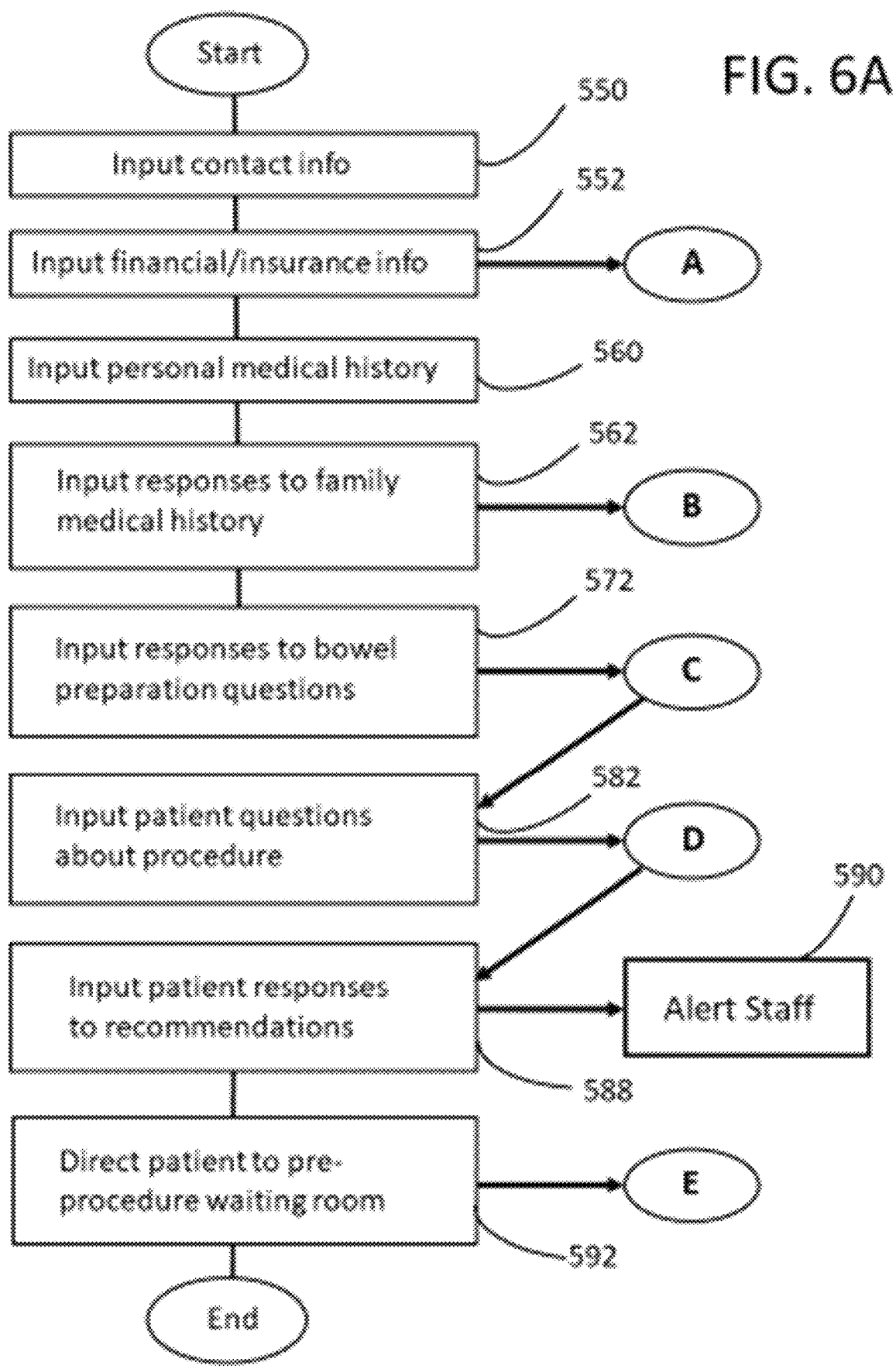
FIGS. 6A through 6G describe an automated workflow for an endoscopy facility that, in accordance with the principles of the present invention, incorporates decision support software and machine learning capability to throughout the patient intake, examination and post-examination periods.
Figure 6B:
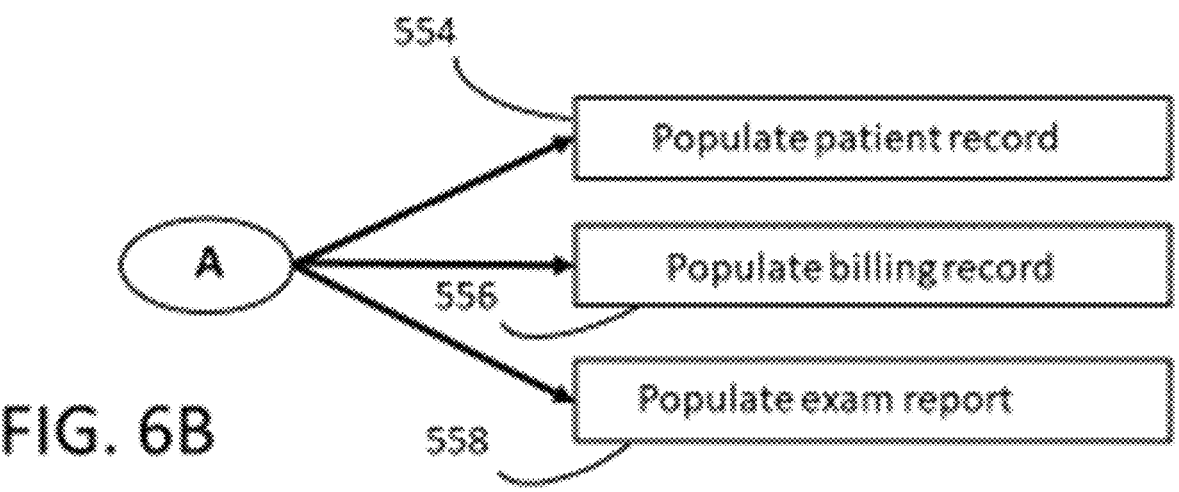

Referring now to FIGS. 6A to 6G, additional details of an automated workflow system and methods for an endoscopy facility of FIG. 5 are described. Advantageously, the process flow in FIG. 6 preferably inform the decision support software and AI/machine learning system that guides the endoscopist during the pre-procedure planning and the endoscopic procedure. In one preferred embodiment, the patient completes an electronic menu-driven questionnaire during patient admission/intake that informs and guides the rest of the procedure. At step 550, the patient inputs his or her contact information, which may include a patient identifier (e.g., account number or social security number) that causes the associated computer to pre-populate other fields in the questionnaire. At step 552, the patient is asked to input or update financial and insurance information, or to confirm the accuracy of any information pre-populated responsive to step 550. As shown in FIG. 6B, responsive to the information input at step 552, the computer may populate other fields in the patient record, step 554, begin populating the billing record for the patient at step 556 and begin populating the examination report for the procedure with patent identification information, at step 558.

Figure 6C:
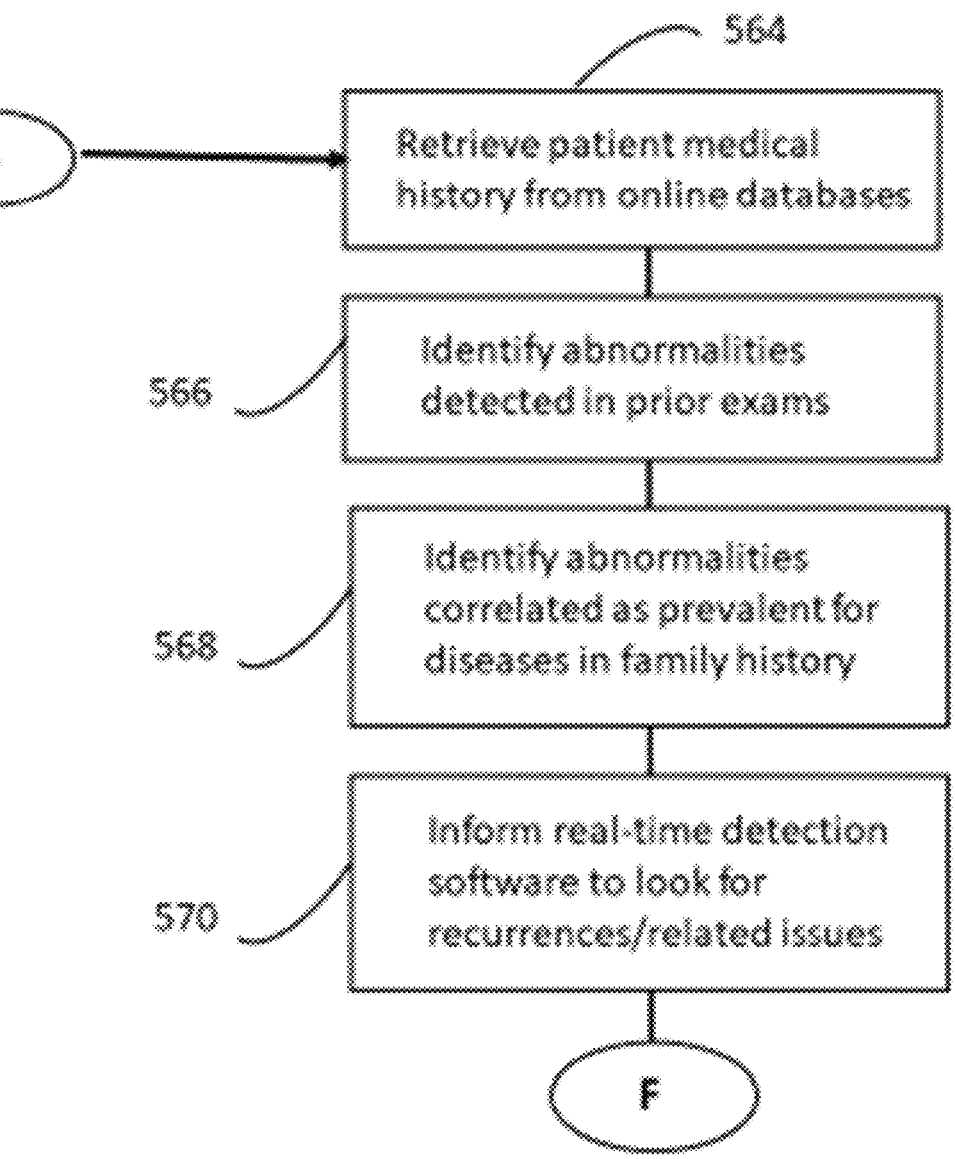
Figure 6D:
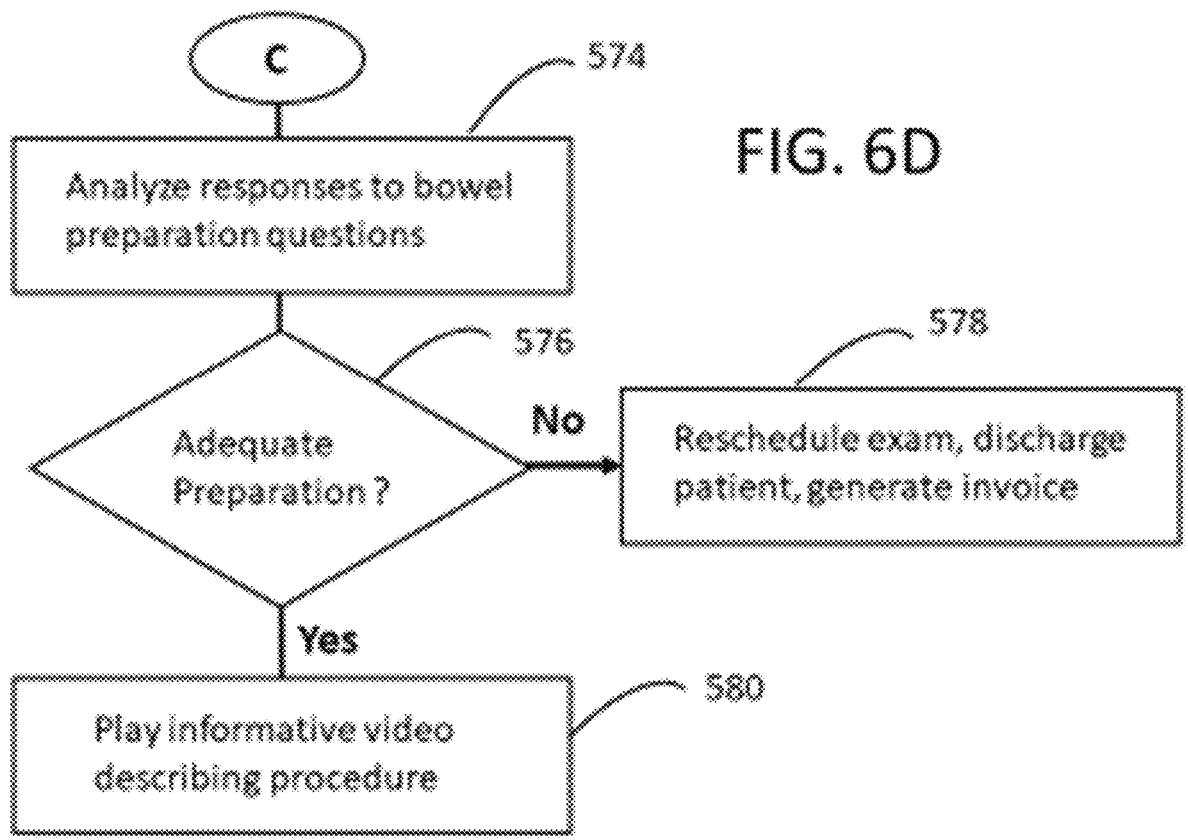
Figure 6E:
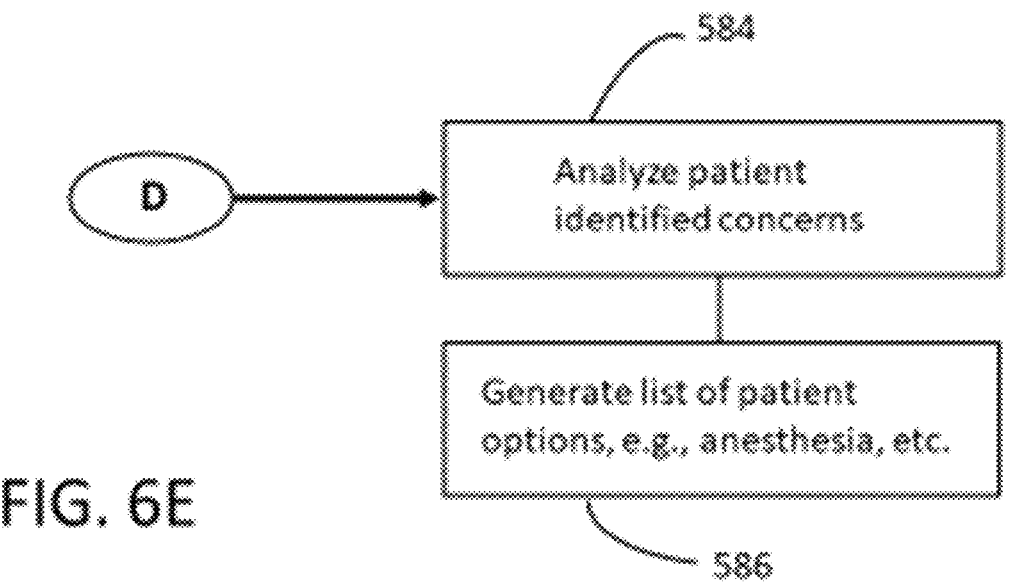

Referring again to FIG. 6A, the patient then inputs information regarding medical history, at step 560, and optionally may input information regarding medical history of blood relatives, at step 562. In one embodiment, as indicated in FIG. 6C, the patient's medical history and family medical history information then is used to retrieve the patient's medical history from related on-line databases. The information retrieved at step 564, is used at step 566 to identify abnormalities detected in prior examinations, while family medical history information input at step 562 is used to identify abnormalities detected in family members, step 568. This information in turn is employed, at step 570, to inform the real-time detection software that will be used during the endoscopy procedure to weight potential occurrence of such prior abnormalities in the detection criteria to be used for the current examination. Advantageously, in this manner, the detection system that provides guidance to the endoscopist during the procedure can be specifically fine-tuned for the patient, thereby reducing the risk that potential abnormalities will go undetected.

Referring to FIG. 6A, at step 572, the patent is presented via the electronic questionnaire with a series of questions regarding the patient's compliance with the bowel cleansing preparation guidelines. As indicated in FIG. 6C, the patient's responses to the bowel preparation guideline compliance questions are analyzed, at step 574, and if the preparation is determined to be inadequate, at step 576, the patient may be informed that the scheduled procedure cannot go forward. In such a case, at step 578, the current appointment will be canceled; the patient will be given an option to reschedule for a later date. The patient then is discharged and an invoice generated for the canceled appointment. If, on the other hand, it is determined that the patient's preparation is adequate, an informative video about the impending procedure is presented to the patient, at step 580. At the conclusion of the video, questions/FAQs are presented to the patient that solicit any concerns the patient may have regarding the procedure. Control returns to the automated patient questionnaire of FIG. 6A, where, at step 582, the patient identifies any concerns he or she may have regarding the procedure.

At step 588 of FIG. 6A, the patient may type or state by voice any concerns he or she may have above the procedure. That input is analyzed, at step 584 of FIG. 6E, to determine whether there are additional steps that the staff may need to take to prepare the patient for the procedure. For example, if the patient indicates that he or she is nervous, the decision support system may suggest at step 586 that the patient request a sedative and/or anesthesia. A short summary of such options and the possible side effects also may be presented to the patient.

At step 588 of FIG. 6A, the patient is requested to select from amongst the sedation, anesthesia, and other options offered at step 586, to request a consultation with the endoscopist or nursing staff, or to confirm that the patient will proceed without any of the offered options. If sedation, anesthesia or other option is requested by the patient at step 588, the staff is alerted, at step 590, of such elections and the staff prepares the necessary materials to effectuate such elections. For example, if a simple oral sedative is requested, the staff may dispense that medication at the patient's waiting area. As another example, if a patient requests anesthesia, the system may alert the staff to call in an anesthesiologist, and to prepare ECG and pulse oximetry monitoring equipment.

In one embodiment e.g.: of a mobile facility, an anesthesiologist may not be available. Prior to the procedure, the patient is informed of the choices available excluding anesthesia. If a patient requires anesthesia, then the patient is not scheduled for the procedure and may be referred to an alternative site or time at which an anesthesiologist is available. This step minimizes the risk that a patient may present for the procedure which cannot be performed due to the absence of an anesthesiologist.

At step 592, when the patient has completed the intake questionnaire, the patient is directed to the pre-procedure waiting room, for example, via directional arrows on the wall or floor of the facility, or by verbal commands. Once the patient arrives the pre-procedure waiting room, he or she may be directed to change into a surgical gown, take any oral sedative dispensed responsive to the patient's elections, and to await further direction from the staff.

Figure 6F:
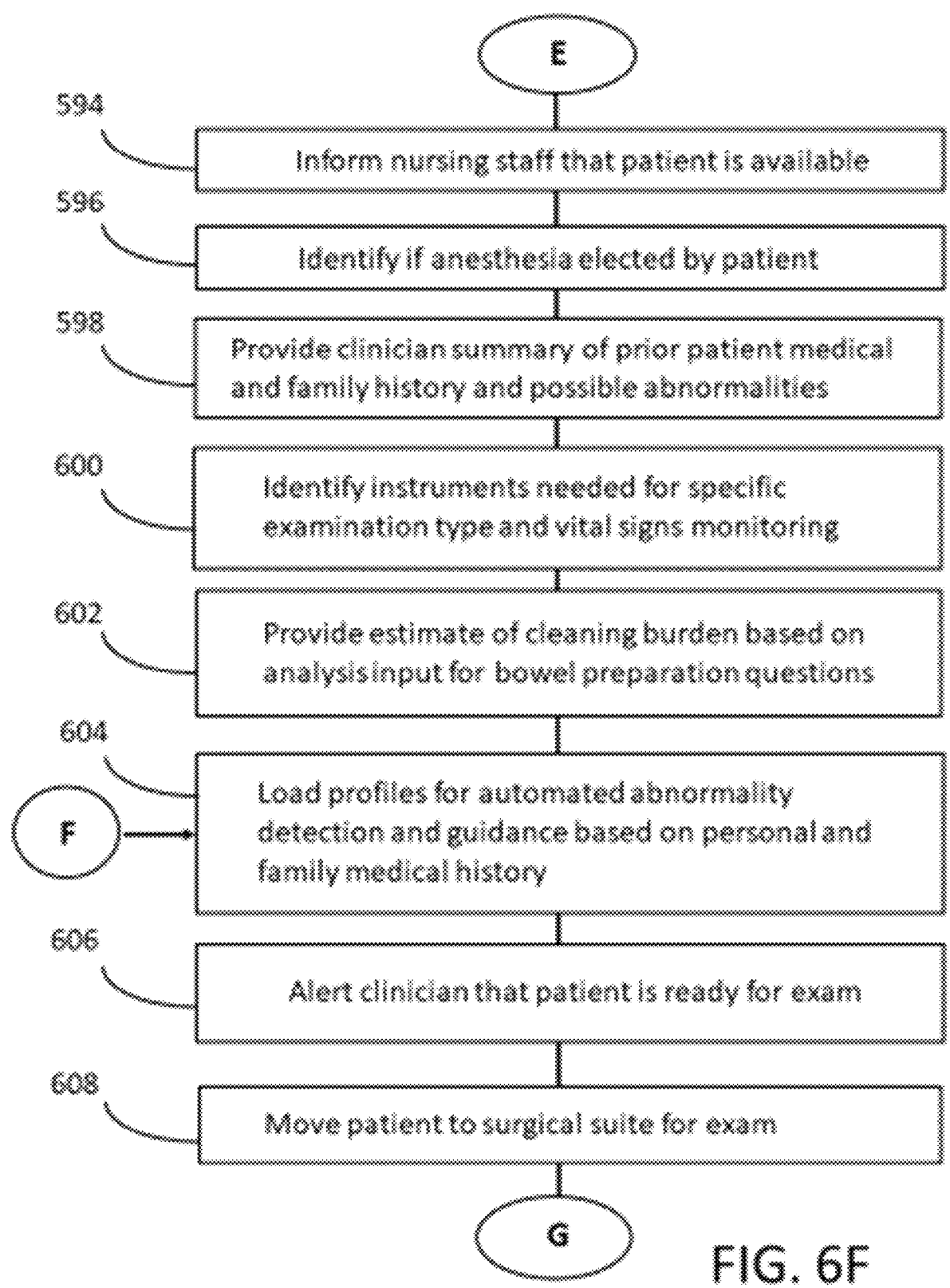

Referring now to FIG. 6F, at step 594 the nursing staff is informed that the patient is available in the pre-procedure room, and at step 596, anesthesia may be administered to the patient. The decision support system, at step 598, responsive to the patient information input into the electronic questionnaire and information retrieved from personal and family medical records, then may present the endoscopist with a summary of the patient's prior medical history and identify possible abnormalities to look for during the procedure. Concurrently, or at the endoscopist's direction, the staff then selects instruments needed for the specific type of endoscopic procedure to be conducted. For example, if the patient's prior examination history indicated the presence of polyps, or resulted in biopsies, biopsy or snare equipment may be retrieved from storage and set out for the endoscopist's use. Additionally, the endoscopist may request that additional vital signs monitoring equipment be positioned in the examination room.

Still referring to FIG. 6F, based on the patient's input to questions regarding compliance with bowel cleansing guidelines, the decision support system may provide an estimate of the cleaning burden that the endoscopist may need to render the patient's large intestine suitable for examination. As described above, a colonoscopy generally is performed by advancing the distal tip of the colonoscopy to the cecum, and then visually inspecting the mucosal surface while the colonoscope is withdrawn. As is generally understood by those of skill in the art, the endoscopist may need to rinse and suction portions of the mucosal surface to remove residual fecal matter and opaque liquid from the colon. Such activity may increase the time allocated to the procedure but is essential to obtaining a thorough examination. Accordingly, having an estimate of the time needed for such activity will assist the endoscopist and staff in preparing subsequent patients who may be waiting in the pre-procedure area.

At step 604, the decision support system may load profiles for automated abnormality detection, and that may be used to guide the endoscopist's movement of the colonoscope, based on the personal and family medical history for the patient. For example, if the patient or a close blood relative previously has been observed to present with polyps or particular types of adenomas, the system may set up to preferentially analyze the video stream generated by the colonoscope to detect such abnormalities. In addition, the overlay of information on monitor 102a (see FIG. 1) may provide a summary of such prior history in a textual format in the margin of the display.

Figure 6G:
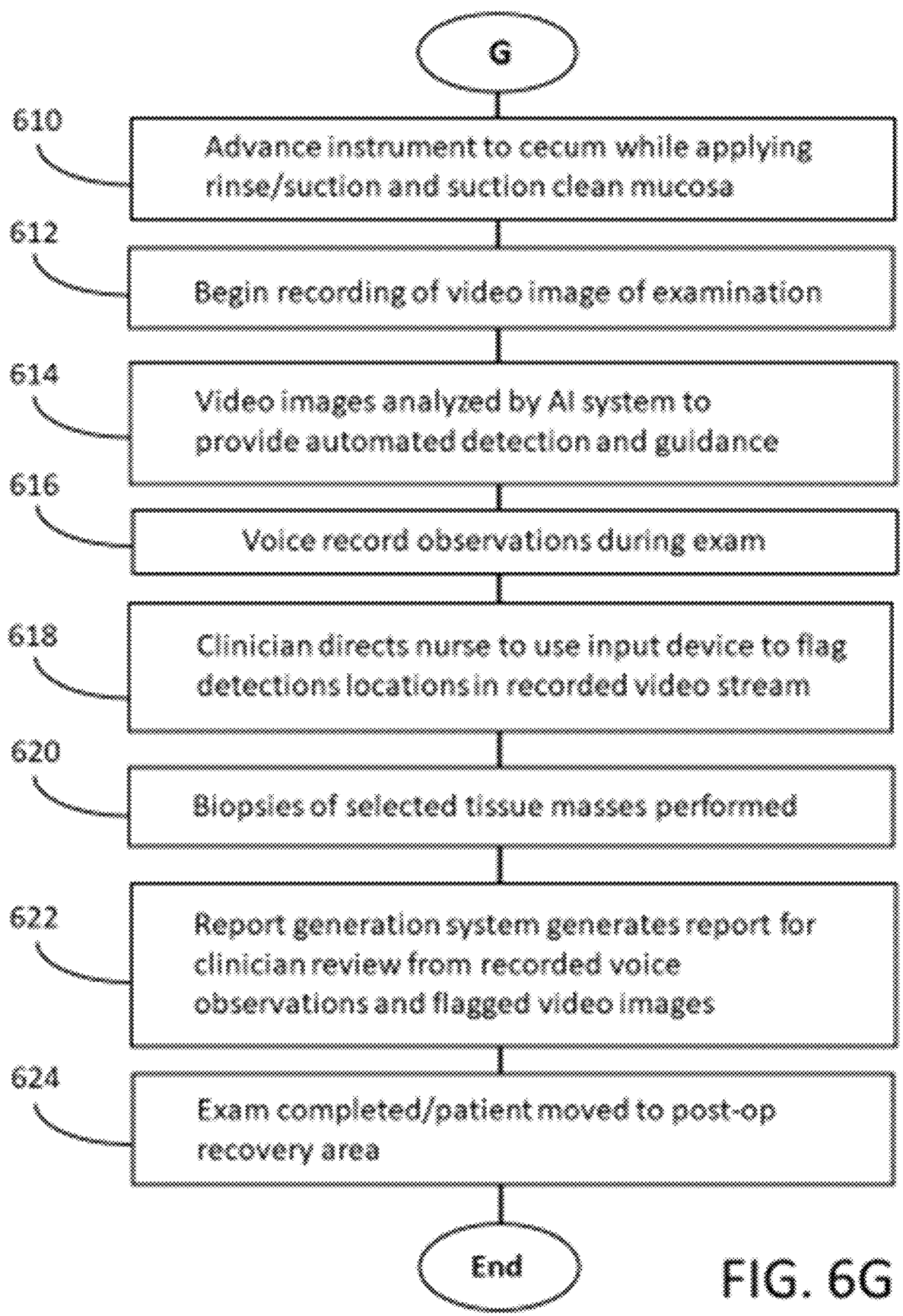

At step 606, the endoscopist is alerted that the patient has been prepared by the staff, e.g., sedated and connected to vital signs monitoring equipment and is ready for the examination. At step 608, the patient is moved to the surgical suite on a gurney. Referring now also to FIG. 6G, at step 610 the endoscopist inserts the endoscope and conducts any cleansing needed to improve visibility. At step 612, the endoscopist or staff initiates recording of the video image generated by the colonoscope. At step 614, the video stream images are analyzed by the AI system, for example, as described in the above incorporated patent application, to provide automated detection and guidance to assist the endoscopist's visual examination of the video image. At step 616, the endoscopist also may make voice recordings of his observations, which are indexed to the video stream. The endoscopist also may direct the nurse to use an input device, e.g., mouse or tablet and pen, to annotate the video stream to flag possible abnormalities for closer re-examination or biopsy during the current procedure or for subsequent examination post-procedure. The endoscopist also may take biopsies of suspicious tissue masses at step 620.

Once the procedure is completed, at step 620, the decision support system generates updates to the exam report that was initiated at step 558 to include a summary of voice comments, flagged annotations and corresponding images captured from the video stream. The video record is made available to the endoscopist for review and approval before it is sent to the referring physician. The entire video log and report then are stored in the health information system database. At step 624, the patient is wheeled on the gurney to the recovery room, and once the anesthesia and/or sedation wears off, is permitted to dress and exist the facility. Selected information from the exam report generated at the conclusion of the procedure, for example, the length of the procedure and number of biopsies, may be used to populate the billing record generated at step 556.

Figure 7:
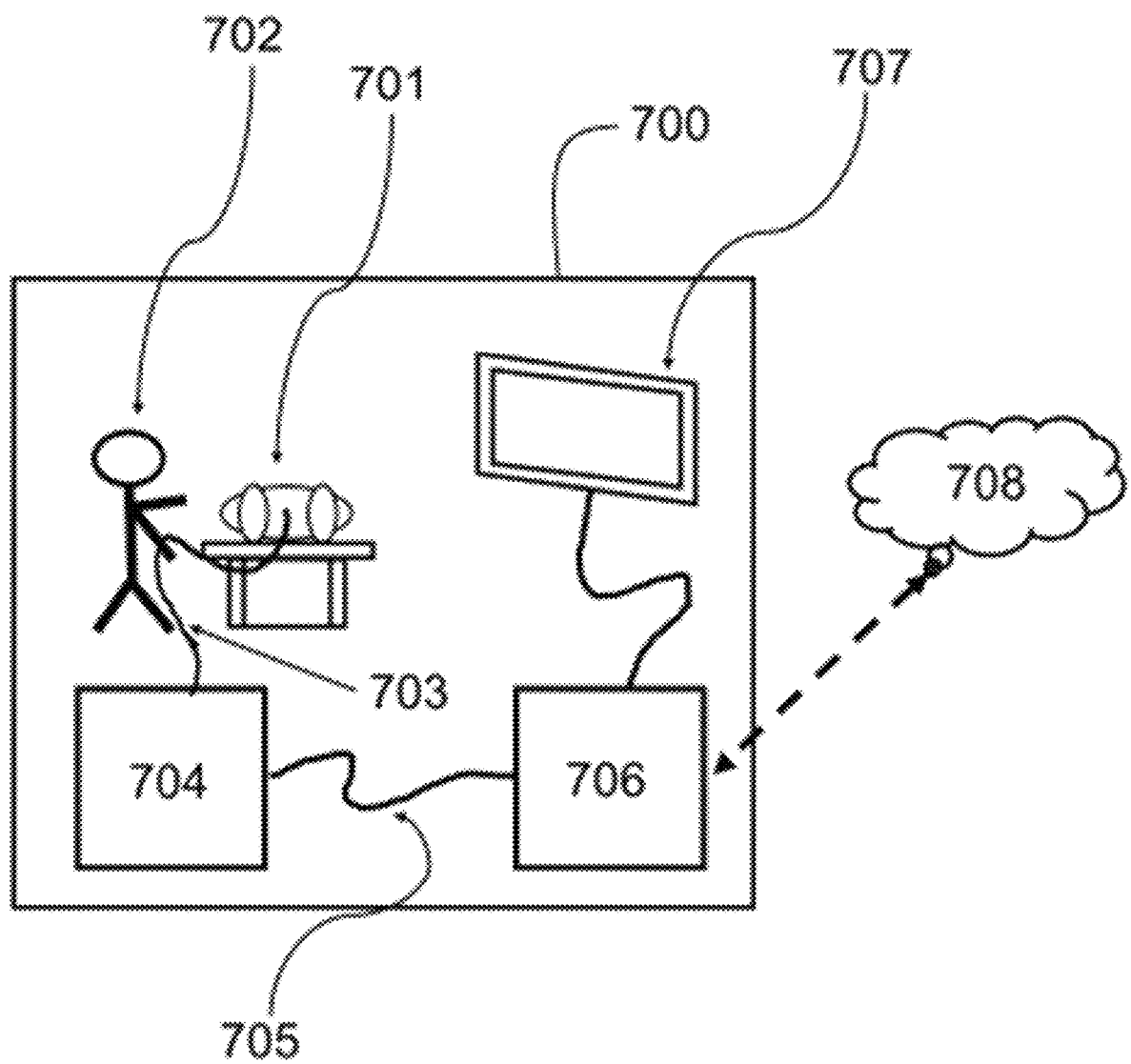
FIG. 7 is a schematic diagram of an alternative endoscopy suite arranged in accordance with the principles of the present invention.

In FIG. 7, an alternative embodiment of an endoscopy suite suitable for implementing the systems and methods of the present invention is described. Endoscopy suite 700 illustratively may be located in a fixed facility or more preferably, a mobile facility. Patient 701 lies on an examination table in an appropriate position. Endoscopist 702 holds and manipulates the endoscope connected via cable 703 (which typically also includes lumens for suction and fluid) to colonoscopy machine 704, available from several manufacturers. The video output from colonoscopy machine 705 is connected to local computer system 706, on which is processed by the artificial intelligence system, as described in the above incorporated co-pending, commonly assigned application. Output from local computer system 706 is displayed on monitor 707, where it is viewed by the endoscopist (and others in the room). In accordance with one embodiment, local computer system 706 is connected to cloud database storage 708 and additional computing resources. Cloud database 708 preferably is connected to the automated patient questionnaire and decision support system described herein above, so that patient information and patient and family medical history data can be retrieved as described with respect to step 564 in FIG. 6C. The results generated during procedure and pathology report described with respect to FIG. 6G also may be stored.

Remote computing resources, e.g. in cloud 708 may continually or episodically examine the image data and patient notes and may use that data to update the machine learning system embodied in local computer 706. In this manner, the performance of the AI assisted endoscopy procedure is continually and automatically improved over time.

Additionally, remote computing resources in cloud 708 may be programmed to monitor the performance of individual endoscopists, for example, by reviewing ADR over time and comparing results from pathology testing with the endoscopists' assignment of pathology status during the procedure. In this manner, the quality metrics of the endoscopy system are recorded, and may be reported as required by law or regulation to health care authorities. Such quality metrics also may be used to report back to each endoscopist on his or her performance, and to provide guidance on potential improvement.

Various general-purpose systems may be used to implement the systems and methods in accordance with the teachings herein. Alternatively, the system made be implemented with more specialized apparatus. Implementation of the inventive features is not limited to any particular endoscope manufacturer, ancillary endoscopy equipment, programming languages, or computer systems. It will be appreciated that a variety of commercially available endoscopy equipment, networking methods, and programming languages may be used to implement the inventive systems and methods.

The system and methods described herein may be provided as a computer program product, or software, that may include a machine-readable medium having stored thereon instructions, which may be used to program a computer system (or other electronic devices) to perform a process according to the present disclosure. A machine-readable medium includes any medium for storing information in a form readable by a machine (e.g., a computer). For example, a machine-readable (e.g., computer-readable) medium includes a machine readable storage medium such as a read only memory ("ROM"), random access memory ("RAM"), magnetic disk storage media, optical storage media, flash memory devices, etc.

It will also be appreciated by one skilled in the art than any data or program storage could be cloud storage, accessible via internet connection such as wireless (Wi-Fi), fixed line (Ethernet) or via the data service on a mobile network.

In addition, it should be understood that steps of the exemplary methods set forth herein may be performed in different orders than presented in this specification. Furthermore, some steps of the exemplary methods may be performed in parallel rather than sequentially. The steps of the exemplary methods may be performed in any suitable location including a hospital, ambulatory surgery center, outpatient clinic, doctor's office, or a mobile facility.

In the foregoing disclosure, embodiments have been described with reference to specific example implementations thereof. It will be evident that various modifications may be made thereto without departing from the broader spirit and scope of the disclosure as set forth in the following claims.

What is claimed is:

1. A system for enhancing detection of tissue abnormalities during an endoscopic procedure, the system comprising:
   an endoscopy system that outputs a video stream during the endoscopic procedure;
   a monitor;
   a database that contains patient specific medical history information comprising previously analyzed video data indicative of previously encountered tissue abnormalities; and
   a processor implementing a patient electronic intake module and an artificial intelligence module,
   wherein, responsive to data input by a patient, the patient electronic intake module transmits patient specific data to the artificial intelligence module; and
   wherein the artificial intelligence module is configured to retrieve the patient specific medical history information from the database based on the patient specific data and to adjust the artificial intelligence module preferentially to analyze the video stream in real-time during the endoscopic procedure to detect features indicative of the tissue abnormalities previously encountered within the patient specific medical history information that correspond to the patient specific data and the patient specific medical history information, the artificial intelligence module generating a composite display comprising the video stream overlaid with graphical information identifying the detected features in the video stream from the endoscopy system indicative of a presence of endoluminal tissue abnormalities.

2. The system of claim 1, wherein the patient specific data comprises patient identification information.

3. The system of claim 1, wherein the features in the video stream indicative of the presence of endoluminal tissue abnormalities are recorded in the patient specific medical history information stored in the database.

4. The system of claim 1, wherein the patient specific data comprises family medical history information for the patient.

5. The system of claim 4, wherein the patient electronic intake module initiates retrieval of patient family medical history information from the database.

6. The system of claim 1, wherein the system further comprises a storage module for recording to the database procedure information about the video stream and overlay generated during the endoscopic procedure.

7. The system of claim 6, further comprising a report generation module, wherein the report generation module selects from the database a subset of the procedure information and formats the subset into a report.

8. The system of claim 1, wherein the patient electronic intake module is configured to present a series of questions to the patient to determine compliance with bowel cleansing guidelines.

9. The system of claim 1, wherein the patient electronic intake module is configured to present an informative video describing the endoscopic procedure and, responsive to patient inputs, present options for sedation or anesthesia.

10. A method for enhancing detection of tissue abnormalities during an endoscopic procedure, the method implemented by a processor executing a patient electronic intake module and an artificial intelligence module for use with an endoscopy system that outputs a video stream during the endoscopic procedure and a monitor, the method comprising:
   by the patient electronic intake module, querying the patient to input data;
   responsive to data input by a patient to the patient electronic intake module, transmitting patient specific data to the artificial intelligence module;
   by the artificial intelligence module, retrieving patient specific medical history information comprising previously analyzed video data indicative of previously encountered tissue abnormalities based on the patient specific data from a database;
   based on the patient specific data and patient specific medical history information, configuring the artificial intelligence module preferentially to analyze the video stream in real-time during the endoscopic procedure to detect features indicative of the tissue abnormalities previously encountered within the patient specific medical history information that correspond to the patient specific data and the patient specific medical history information; and
   generating by the artificial intelligence module a composite display comprising the video stream overlaid with graphical information identifying the detected features in the video stream from the endoscopy system indicative of a presence of endoluminal tissue abnormalities.

11. The method of claim 10, wherein querying the patient to input data comprises querying the patient to input patient identification information.

12. The method of claim 10, wherein the features in the video stream indicative of presence of endoluminal tissue abnormalities are recorded in the patient medical history information stored in the database.

13. The method of claim 10, wherein querying the patient to input data comprises querying the patient to input patient family medical history information.

14. The method of claim 10, further comprising retrieving patient family medical history information from the database responsive to the data input by the patient.

15. The method of claim 10, further comprising recording to the database procedure information about the video stream and overlay generated during the endoscopic procedure.

16. The method of claim 15, further comprising selecting from the database a subset of the procedure information and formatting the subset into a report.

17. The method of claim 10, further comprising, by the patient electronic intake module, presenting a series of questions to the patient to determine compliance with bowel cleansing guidelines.

18. The method of claim 10, further comprising, by the patient electronic intake module, presenting an informative video describing the endoscopic procedure and, responsive to patient inputs, presenting options for sedation or anesthesia.

19. The method of claim 10, wherein machine learning generated algorithms are trained using cross-validation.

\* \* \* \* \*